United States Patent [19]

Speranza et al.

[11] Patent Number: 4,927,942
[45] Date of Patent: May 22, 1990

[54] METHOD FOR THE PREPARATION OF IMIDAZOLES

[75] Inventors: George P. Speranza; Wei-Yang Su, both of Austin, Tex.

[73] Assignee: Texaco Chemical Co., White Plains, N.Y.

[21] Appl. No.: 284,884

[22] Filed: Dec. 15, 1988

[51] Int. Cl.$^5$ ............................................. C07D 233/58
[52] U.S. Cl. ................................. 548/335; 548/346
[58] Field of Search ............................... 548/335, 346

[56] References Cited

U.S. PATENT DOCUMENTS

| | | | |
|---|---|---|---|
| 2,399,601 | 4/1946 | Kyrides et al. | 548/335 |
| 2,404,299 | 7/1946 | Kyrides | 548/335 |
| 2,847,417 | 8/1958 | Erner | 548/335 |
| 2,891,966 | 6/1959 | Vesely et al. | 549/86 |
| 3,037,028 | 5/1962 | Green | 548/335 |
| 3,152,998 | 10/1964 | Moss | 544/358 X |
| 3,255,200 | 6/1966 | Green | 548/335 |
| 3,715,365 | 2/1973 | Schulze | 548/335 |
| 4,340,744 | 7/1982 | Schwarz | 548/346 |
| 4,409,389 | 10/1983 | Bellas et al. | 548/342 |
| 4,436,892 | 3/1984 | Zondler et al. | 528/117 |

FOREIGN PATENT DOCUMENTS 3009605 10/1981 Fed. Rep. of Germany .

OTHER PUBLICATIONS

*Chemical Abstracts* 61:13317f, (1964), [FR. 1,362,689, 6/5/64].
B. Radziszewski, *Berichte,* 15,2706, (1882).
B. Radziszewski, *Berichte,* 16,487, (1883).
R. Weidenhagen et al., *Berichte,* 72,57, (1939).
WPI Abstract of Ols 1,952,991.
*Chemical Abstracts* 70:28867g, (1969), [N. Sawa, *Nippon Kagaku Zasshi,* 1968, 89(9), 868–72].

*Primary Examiner*—Richard A. Schwartz
*Attorney, Agent, or Firm*—Jack H. Park; Kenneth R. Priem; Cynthia L. Kendrick

[57] ABSTRACT

This invention discloses an improvement in the method for preparation of imidazoles by dehydrogenation of imidazolines over a nickel catalyst comprising reacting the imidazoline over a nickel catalyst in combination with from 2 to 30 weight percent of a catalyst from the group consisting of copper, chromium or a combination of both at a temperature of 160° C. to 250° C. and a pressure of atmospheric to 500 psig.

13 Claims, No Drawings

METHOD FOR THE PREPARATION OF IMIDAZOLES

CROSS-REFERENCE

This application is related to U.S. application Ser. No. 284,883, filed of even date.

FIELD OF THE INVENTION

This invention relates to an improved method for preparation of imidazoles. More particularly, this invention relates to a method for the selective preparation of imidazoles by dehydrogenation of imidazolines to imidazoles over a catalyst comprising nickel in combination with specific proportions of one or more transition metals at mild temperatures and atmospheric pressure.

Unexpected advantages are observed by virtue of the fact that very high yields and essentially no by-products are obtained where the catalyst comprises copper and/or chromium combined with nickel using milder conditions than are used in related art.

BACKGROUND OF THE INVENTION

Imidazoles and simple imidazole derivatives are being used more and more as hardening agents for epoxy resins. They provide long pot life, high heat distortion temperatures, economical performance based on low PHR requirements and lower toxicity than amines. They are useful accelerators (catalysts) for anhydride cure and bisphenol-A cure of epoxy resins. The imidazole ring can be utilized in numerous reactions and these derivatives can be used for specialty epoxies. For example, delayed action can be obtained by acylating imidazoles with polychlorinated benzoyl chloride. See U.S. Pat. No. 4,436,892.

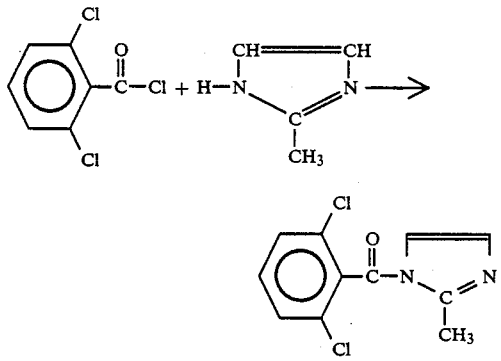

Early synthesis of imidazoles involved the reaction of 1,2-dicarbonyl compounds with ammonia and aldehydes to produce low yields according to the equation:

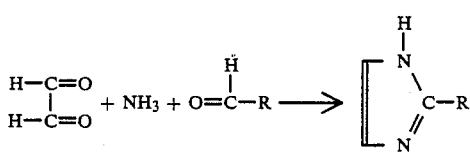

The yields were increased when the reaction was carried out in organic acids with ammonium acetate. Radziszewski, R. Ber., 15, 2706 (1882).

Imidazole oxalate, fumarate, adipate and phthalate and 4-methylimidazole, 4,5-dimethylimidazole and 2-isopropylimidazole have been made from the $\alpha,\beta$-dicarbonyl compounds, as demonstrated in U.S. Pat. No. 3,715,365.

Werdenhazen, R., and Rienacker, H., Ber. 72, 57 (1939) demonstrated the production of imidazoles from $\alpha$-hydroxyketones under the influence of ammoniacal cupric acetate and aldehydes represented by the following:

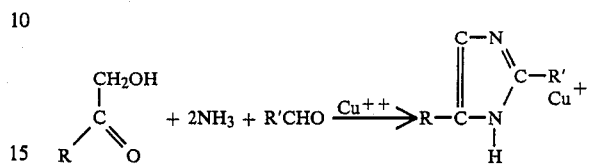

In "New Methods of Preparative Organic Chemistry", Vol. 3, p. 241, Academic Press. N.Y., 1964, H. Budereck, et al. describe another method involving formamide synthesis according to the equation:

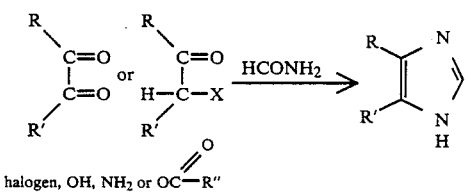

X = halogen, OH, $NH_2$ or $OC-R''$

Some 2-methylimidazoles have been prepared using acetamides; however, yields were reduced when amides other than formamide were used.

One of the more attractive methods for producing imidazoles is discussed in U.S. Pat. No. 2,891,966. This involved the reaction of a 1,2-diamine with carboxylic acids. For instance, ethylene diamine was admixed with a slight excess of acetic acid, permitting an exothermic rise which dissolved the reagents. The homogeneous solution was cooled to about 100° C., then charged through a continuous reactor equipped with a preheater section, a reactor section filled with platinum. Then the reactor was heated to 430° C. and hydrogen added. The vaporous reaction effluent was condensed to obtain crystalline 2-methyl imidazole.

A French patent describes the purification of 2-methyl imidazole by codistilling it with 1- or 2-methylnaphthalene and then washing with pentane or toluene. See French P. No. 1,362,689 (1964).

In other work, the diamine is converted to 2-alkyl imidazoline, and then dehydrogenated to the corresponding imidazole compound by dehydrogenation over a nickel catalyst. For example see U.S. Pat. Nos. 2,399,601 and 2,404,299 on the preparation of imidazoles by heating imidazolines with Raney nickel catalysts. The reactions were carried out at 225°-235° C. The yields were not reported in some cases or varied widely.

H. A. Green, of Air Products has demonstrated that 1,2-diamines can be reacted with aldehydes and then heated over a platinum-alumina catalyst at 370° C. to give imidazoles. In the case of ethylenediamine and propionaldehyde a 56% yield of 2-ethyl imidazole was obtained. See U.S. Pat. No. 3,037,028, May 29, 1962.

In U.S. Pat. No. 3,037,028, using another vapor phase reaction, Green demonstrated that imidazole could be obtained from ethylenediamine and formamide using a large volume of hydrogen. See also U.S. Pat. No.

3,255,200. The catalyst used was platinum-on-alumina and alumina or cobalt molybdate were shown to be ineffective. Treating ethylenediamine with methyl formate at 25°–30° C. gave 98.5% diformyl derivative.

In Ger. Offen. DE No. 3,009,605, diformyl derivative was passed with nitrogen over 6:14 NiO:MoO₃ at 400° C. to give 65.7% imidazole with 99.3% conversion. The yield remained constant after 250 hours use of the catalyst.

Imidazolines can be dehydrogenated to imidazoles at 250°–500° C. over MoO₃ and NiO and/or CoO and Al₂O₃, SiO₂ and/or alkaline silicate catalysts. See DE No. 3,009,631. This reaction has been used to make a variety of 2-alkylimidazoles substituted with long chain fatty acids. As noted, the minimum temperature requirement is 250° C.

Another route to imidazoles involved the reaction of a nitrile with a diamine over a copper salt to give imidazolines which were then dehydrogenated with an aluminum-zinc oxide catalyst to give imidazoles. See DE No. 3,236,598-A to BASF.

In U.S. Pat. No. 4,409,389, hexamethylene-tetramine was reacted with formamide at 140° C. to give a bis-formamide. The bis-formamide with dicarbonyl compounds and 2 moles of mineral acid yields imidazole acid salts.

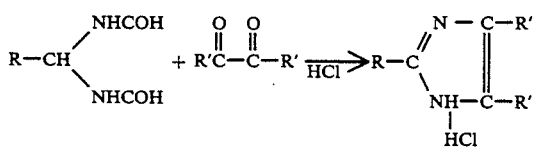

In Ger. Offen. No. 1,952,991, imidazole was made in 53% yield by passing a solution of ethylenediamine and formic acid over a Cd-Cu chromite catalyst at 480° C. This method required quite high temperatures and the yield was very moderate.

Imidazolines have been dehydrogenated with sulfur, manganese dioxide, etc.

It is noted that most methods for producing imidazoles which are found in the art require higher temperatures and the yields reported are nowhere near 99%. Further one does not observe the higher yields and mild temperatures in the same work. For instance, no previously used process for producing imidazoles allows for as great as 99% yield or higher with almost no by-products using temperatures of around 200° C. or less.

It would be a substantial advance in the art if imidazoles could be prepared in essentially quantitative yields using mild conditions. Such a process would be particularly attractive economically if essentially no by-products were formed.

SUMMARY OF THE INVENTION

In accordance with the foregoing, the present invention provides a method of preparing imidazoles by dehydrogenation of imidazolines over a catalyst comprising nickel in combination with one or more transition metals, preferably copper and/or chromium, at a temperature of 160° C. to 250° C. and a pressure of atmospheric to 500 psig. As will be demonstrated in the Examples the particular combination in the catalyst of this invention demonstrated substantially higher yields using milder conditions.

Imidazoles and imidazole derivatives may be used as hardening agents for epoxy resins. They provide long pot life, high heat distortion temperatures, economical performance based on low PHR requirements and lower toxicity than amines.

DETAILED DESCRIPTION OF THE INVENTION

This invention describes a selective process for the preparation of imidazoles. According to the invention, imidazolines can be reacted over dehydrogenation catalysts comprising nickel in combination with copper and/or chromium. The imidazole products can be derived in high yield at mild conditions without the formation of by-products.

The imidazolines which are reacted over the dehydrogenation catalyst preferably are of the following structure:

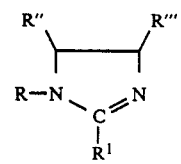

where R is H or an alkyl group containing 1–18 carbon atoms; R¹ is H, an aromatic or an alkyl group containing 1 to 17 carbon atoms; R'' is H or an alkyl group containing 1–4 carbon atoms; and R''' is H or an alkyl group containing 1–4 carbon atoms.

Suitable imidazolines can be obtained from several sources. For example, imidazolines can be produced from organic acids and diamines. Examples include 2-heptadecenyl-1-isopropylimidazoline prepared from oleic acid and N-isopropylethylene diamine, and 1-isopropyl-2-methyl imidazoline prepared from acetic acid and N-isopropylethylenediamine.

Other imidazolines which provide suitable reactants in the process of this invention include 1-isopropyl-2-methylimidazoline, 2,4-dimethylimidazoline, imidazoline, 2-methylimidazoline and 1-methylimidazoline.

The catalyst employed for dehydroqenation of imidazolines comprises nickel in combination with one or more transition metals, preferably copper and/or chromium. In other work nickel catalysts have been used as dehydrogenation catalysts, however, it has been surprisingly discovered in the instant invention that the use of one or more additional transition metals in combination with nickel allows the use of much lower temperatures and permits much higher conversions and yields with very minimal or no by-products. These features are very attractive for commercial reasons.

Transition metals which can be used in conjunction with the nickel include manganese, iron, zinc, copper and chromium. The preferred catalyst was obtained where the nickel was combined with copper or chromium or both.

The quantity of nickel compound and copper or chromium employed in the catalyst may vary. The reaction proceeds when employing as little as about 50 per cent of nickel together with about 0 weight percent of copper and 0% chromium, basis the total weight of the catalyst. The percentage of copper and/or chrome should be about 2 to about 30%. From 70 to about 80 wt % of nickel in conjunction with from about 20 to 30 of copper and/or chromium is generally desirable. A preferred catalyst is one described in U.S. Pat. No. 3,152,998. Suitable catalysts include 70 98 weight percent nickel in combination with from 2 from 30 weight percent metals from the group consisting of copper, chromium or a combination thereof; 70 95 weight percent nickel and from 5 to 30% copper-containing compound; 80 to 99 percent nickel in combination with 1 to 20% chromium; 60 to 80% nickel, 14 to 37% copper and 1 to 5% chromium; 72 to 78%, 20 25% copper and 1 to 3% chromium; 95 to 99.8% nickel and 0.2 to 5% chromium.

The temperature range which can usefully be employed is variable depending upon other experimental factors, including the pressure and the choice of particular species of catalyst among other things. The range of operability is from about 150° C. to 300° C. A narrow range of 160° to 250° is preferred and reflects significantly milder temperatures than previously used in the art. A suitable temperature range is 190° C. to 220° C.

Pressures of subatmospheric to 500 psig can be used. Substantial yields are realized using atmospheric pressure.

The products are imidazoles having the general structure:

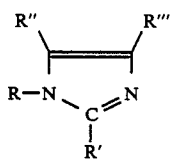

where R is H or an alkyl group containing 1–18 carbon atoms; R' is H, an aromatic or an alkyl group containing 1 to 17 carbon atoms; R" is H or an alkyl group containing 1–4 carbon atoms; and R''' is H, or an alkyl group containing 1–4 carbon atoms.

These imidazole and simple imidazole derivatives are being used more as hardening agents for epoxy resins. They provide long pot life, high heat distortion temperatures, economical performance based on low PHR requirements and lower toxicity than amines. They are useful accelerators (catalysts) for anhydride cure and bisphenol -A cure of epoxy resins. The imidazole ring can be utilized in numerous reactions and these derivatives can be used for specialty epoxies.

Specific products demonstrated in this invention include 1-isopropyl-2-methylimidazole, 2,4(5)-dimethylimidazole, 2-heptadecenyl-1-isopropylimidazole and 2-heptadecenylimidazole.

The process can be conducted in a kettle, tubular reactor or a glass reactor. The catalyst may be initially introduced into the reaction zone batchwise, or it may be continuously or intermittently introduced into such a zone during the course of the synthesis reaction. Operating conditions can be adjusted to optimize the formation of the desired imidazole products. The product is recovered preferably by fractional distillation.

The products have been identified by one or more of the following analytical procedures, viz, gas-liquid chromatograph (glc), infrared (IR), nuclear magnetic resonance (nmr) and mass spectra or a combination of these techniques. Analyses have, for the most part, been by parts in weight; all temperatures are in degrees centigrade and all pressures in pounds per square inch gauge (psig). The selectivity means the moles of imidizole produced divided by moles of imidizoline.

Various embodiments of the process of this invention are illustrated in the following examples which are not to be considered limitative:

EXAMPLE 1

Preparation of 1-Isopropyl-2 -methylimidazole

A 100-ml three-necked flask equipped with a thermometer, condenser, magnetic stirrer, and nitrogen inlet was charged with 1-isopropyl-2-methylimidazoline (50 g, 0.4 mole) and nickel-copper-chromium catalyst (5.0 g) as described in U.S. Pat. No. 3,152,998. The reaction was carried out at 200° C. with stirring and under a nitrogen atmosphere for about 5 hours. GLC analysis showed that more than 99% of the starting imidazoline had been converted to give the corresponding imidazole with 98.5% selectivity. The product was fractionally distilled under reduced pressure (80° C. at 1.2 mm Hg) to give a clear, colorless liquid in about 98% yield.

EXAMPLE 2

Preparation of 2,4(5)-Dimethylimidazole

The procedure of Example 1 was followed except that 58.9 g of 2,4-dimethylimidazoline and 5.8 g of the same catalyst used in Example 1 were charged. GLC analysis showed that a 96% yield of 2,4(5)-dimethylimidazole and 3% yield of imidazole isomers were obtained.

EXAMPLE 3

Preparation of 2-Heptadecenyl-1-isopropylimidazole

A 100-ml three-necked flask equipped with a thermometer, condenser, magnetic stirrer and nitrogen inlet was charged with 50 g of 2-heptadecenyl-1-isopropylimidazoline (prepared from oleic acid and N-isopropylethylene diamine) and 5.0 g of nickel-copper-chromium catalyst as used in Example 1. The reaction was carried out at 200° C. with stirring and under a nitrogen atmosphere for about 7 hours. The product was analyzed by $C^{13}$, NMR and IR and found to be almost all 2-heptadecenyl-1-isopropyl imidazole.

EXAMPLE 4

Preparation of 2-Heptadecenylimidazole

The procedure of Example 3 was followed except that 48.9 g of 2-heptadecenyl imidazoline (prepared from oleic acid and ethylenediamine) and 5.0 g of the same nickel-copper-chromium catalyst were charged. The product was analyzed by $C^{13}$, NMR and IR and found to be almost all 2-heptadecenylimidazole. The yield was almost quantitative.

EXAMPLE 5

Raney Ni Catalyst

The procedure of Example 1 was followed except that 40 g of 1-isopropyl-2-methylimidazoline and 5 g of Raney nickel were charged. GLC analysis showed that an 84% yield of 1-isopropyl-2-methyl imidazole was obtained with 98% conversion of imidazoline.

EXAMPLE 6

Cobalt Catalyst

The procedure of Example 1 was followed except that 26.2 g of 1-isopropyl-2-methylimidazoline and 3.0 g of a cobalt hydrogenation catalyst was charged. GLC analysis show that a 14% yield of 1-isopropyl-2-methylimidazole was obtained with 19% conversion of imidazoline.

EXAMPLE 7

Raney Ni-Cr

The procedure of Example 1 was followed except that 50.0 g of 1-isopropyl-2-methylimidazoline and about 5 g of Raney Nickel-chromium catalyst was charged. GLC analysis showed that 98% yield of 1-isopropyl-2-methylimidazole was obtained with >99% conversion of imidazoline.

What is claimed is:

1. In a method for preparation of imidazoles by dehydrogenation of imidazolines over a nickel catalyst, the improvement comprising reacting the imidazoline over a catalyst selected from the group consisting of nickel-copper, nickel-chromium and nickel-copper-chromium at a temperature of 160° C. to 300° C. and a pressure of atmospheric to 500 psig.

2. The method of claim 1 wherein the imidazoline reactant has the structure:

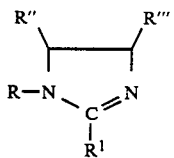

wherein R is H or an alkyl group containing 1 to 18 carbon atoms, $R^1$ is H or an aromatic or alkyl group containing 1 to 17 carbons, R" is H or an alkyl group containing 1-4 carbon atoms, and R''' is H or an alkyl group containing 1-4 carbon atoms.

3. The method of claim 1 wherein the catalyst comprises nickel in combination with copper.

4. The method of claim 1 wherein the catalyst comprises nickel in combination with chromium.

5. The method of claim 1 wherein the catalyst comprises nickel in combination with mixed copper and chromium.

6. The method of claim 1 wherein the catalyst consists of from 70 to 98 weight percent nickel in combination with from 2 to 30 weight percent metals from the group consisting of copper, chromium or a combination thereof.

7. The method of claim 3 wherein the catalyst comprises 70 to 95 weight percent nickel and from 5 to 30% copper-containing compound.

8. The method of claim 4 wherein the catalyst comprises 80 to 99 percent nickel in combination with 1 to 20% chromium.

9. The method of claim 5 wherein the catalyst comprises 60 to 80% nickel, 14 to 37% copper and 1 to 5% chromium.

10. The method of claim 1 wherein the catalyst comprises 72 to 78% nickel, 20 to 25% copper and 1 to 3% chromium.

11. The method of claim 1 wherein the catalyst comprises 95 to 99.8% nickel and 0.2 to 5% chromium.

12. The method of claim 1 wherein the temperature is from 190° C. to 220° C.

13. The method of claim 1 wherein the pressure is at or near atmospheric pressure.

* * * * *